United States Patent
Cho et al.

(10) Patent No.: US 6,349,740 B1
(45) Date of Patent: Feb. 26, 2002

(54) MONOLITHIC HIGH PERFORMANCE MINIATURE FLOW CONTROL UNIT

(75) Inventors: Steve T. Cho, Santa Clara; Harlow B. Christianson, San Jose, both of CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/288,762

(22) Filed: Apr. 8, 1999

(51) Int. Cl.[7] .......................... F16K 31/02; G01N 27/26
(52) U.S. Cl. .................... 137/487.5; 137/807; 137/827; 251/129.01; 204/601
(58) Field of Search .............................. 137/487.5, 807, 137/827; 251/129.01; 204/601; 604/891.1

(56) References Cited

U.S. PATENT DOCUMENTS

| | | | | |
|---|---|---|---|---|
| 4,203,398 A | * | 5/1980 | Marouka | 137/807 |
| 5,377,721 A | * | 1/1995 | Kiyohiro et al. | 137/827 |
| 5,417,235 A | * | 5/1995 | Wise et al. | 251/129.01 |
| 5,785,831 A | * | 7/1998 | Bek | 204/451 |
| 5,992,820 A | * | 11/1999 | Fare et al. | 251/129.01 |

FOREIGN PATENT DOCUMENTS

JP 406081816 * 3/1994 ............ 251/129.01

* cited by examiner

Primary Examiner—Michael Powell Buiz
Assistant Examiner—Ramesh Krishnamurthy
(74) Attorney, Agent, or Firm—Beth A. Vrioni

(57) ABSTRACT

A monolithic flow controller for controlling the rate at which a medicinal liquid is administered to a patient. The monolithic flow controller includes one or more virtual valves that, because of their relatively small opening size (less than 0.5 $\mu$m in diameter), only permit fluid to flow through the valve when a forward bias voltage is applied. If a reverse bias voltage or no voltage is applied, fluid flow through the opening is inhibited. The fluid rate through the device is monitored using two pressure sensors or a differential pressure sensor that determine the differential pressure along the flow path through the device or relative to the external ambient pressure. The flow through the device is equal to the product of the differential pressure and the conductance of the channel in the flow controller. A capacitive bubble sensor is optionally provided to detect bubbles in the medicinal liquid being administered to the patient. The flow controller can be made sufficiently small to be injected into a patient's cardiovascular system or other portion of the patient's body through a hypodermic syringe and needle, or it can be implanted in the patient's body at a desired site. The medicinal liquid can be contained within an integral pressurized fluid reservoir, administered by gravity feed, or conveyed by a pump to an inlet port of the flow controller.

20 Claims, 6 Drawing Sheets

MONOLITHIC HIGH PERFORMANCE MINIATURE FLOW CONTROL UNIT

FIELD OF THE INVENTION

The present invention generally relates to a flow control that includes a flow sensor, and more specifically, to a micro/miniature flow control in which an electric potential is employed to control fluid flow through the device.

BACKGROUND OF THE INVENTION

Fluid control in portable and implantable medical devices typically requires techniques be employed that are uniquely suited to micro/miniature fluid circuits. For example, conventional mechanical or electromechanical valves are too large and often too slow to be used in such applications. Other types of fluid valves require more space than is available in micro/miniature fluid circuits. Examples of mechanical valves and some of their characteristics and limitations are: shape memory alloy actuated valves (actuated by changes in temperature, but subject to fatigue failure), thermopneumatically actuated valves (typically electrochemically activated—may require several minutes to respond and are temperature sensitive), bi-morph (Al/Si) (reliability problems and typically capable of less than 1 mm stroke), Ni—Si based valves (thermally activated and typically capable of less than 1 mm stroke), mini-solenoid actuated valves (good reliability and relatively small stroke), and electrostatic valves (very reliable and characterized by short actuation distance). The various types of mechanical valves listed above require an area of at least 4 mm×4 mm, which is much more than is generally available in a micro/miniature fluid circuit. While micromechanical valves are available that are smaller than the conventional mechanical valves discussed above, such valves are typically designed to control gas flow by moving a membrane over an orifice and are generally not suitable for controlling the flow of a liquid.

A more suitable type of valve for micro/miniature fluid circuit applications, because it requires much less area to operate, is sometimes referred to as a "virtual valve." Traditional valves have moving components that regulate flow. A virtual valve has the same characteristics of a mechanical valve, except that there are no moving parts in a virtual valve. Virtual valves take advantage of microfluidic characteristics such as surface tension or pressure gradients to regulate fluid flow. Some virtual valves employ an externally applied pressure to move fluid. Pressure balanced virtual valves may also employ external pneumatic pressure or convert kinetic energy to pressure, but tend to be dependent upon channel shape. Bubble valves are another type of virtual valve that are designed to generate bubbles to block fluid flow by creating temperature gradients. Pressure balanced virtual valves serve the function of dual check valves in pumping circuits and may comprise pairs of tapered channels (with the tapers directed in opposite directions) that tend to permit fluid flow in one direction, but not the other. Although pressure balanced valves have an advantage because they do not require moving parts, they are not leak free, and fluid flow is usually not symmetric through the pairs of tapered channels.

It may be necessary to monitor fluid flow in a microfluid circuit. Often, due to the small size of the passages in such devices, the rate of fluid flow is too low to be measured by conventional flow sensors. For example, a thermal flow sensor does not have sufficient sensitivity to monitor flow rates less than 1.0 ml/hr. In some applications, the rate of flow is measured in $\mu$l/hr., which is far below the range of mechanical flow sensors. The typical full-scale range for a micro/miniature flow sensor is three orders of magnitude higher than the required accuracy. Most flow sensors currently used for such applications are of the thermal sensor type in which the temperature is measured around a heated element to determine the rate of fluid flow as a function of heat dissipated in the fluid flowing past the element. Another thermal flow measurement technique applies heat pulses to an element disposed in a fluid channel; the phase shift of the first harmonic of the temperature pulses is inversely proportional to the flow velocity of fluid past the element. Pressure based flow sensors apply the Bernoulli principle and use capacitive or resistive elements, drag force sensors, anemometers, acoustic Doppler sensors, and Coriolis sensors. Each type of flow sensor has desirable virtues, but most are not suitable for monitoring low fluid flow in micro/miniature fluid circuits, either because of their lack of sensitivity, slow response time, excessive size, or because they require excessive power.

Bubble sensors are also often required in medical infusion pumps to monitor the quality of liquids being infused into a patient. The techniques typically used for sensing bubbles in a fluid stream detect the bubbles by sensing changes in acoustic signals propagated through the liquid, changes in a permitivity measured across the liquid stream, variations in an optical light path, or changes in the output of a hydrophone sensor. Not all of these techniques are particularly applicable to micro/miniature fluid circuits because of size limitations. For example, the piezoelectric transducers used for generating and receiving sound waves transmitted through a fluid stream are not readily produced in micro/miniature size. Sensing bubbles by their effect on light passing through a fluid stream requires little power and has a fast response time, but may not work well if the liquid is opaque. Hydrophones are generally too large and require too much complexity in the required supporting electronics to be practical for detecting bubbles in micro/miniature fluid circuits. Capacitive bubble sensors are relatively simple, comprising two spaced-apart metal plates disposed on opposite sides of a liquid path in the fluid circuit, for sensing changes in permitivity occurring when a bubble passes between the plates.

Applications for micro-miniature fluid control circuits include medical apparatus, such as implantable liquid metering infusion systems and pump cassettes, for administering drugs and other medicinal fluids. Such fluid control circuits are also usable in gravity fed tube sets for infusing liquids into a patient's cardiovascular system. The size of portable devices of this type that are self-contained (i.e., not coupled to an external fluid source) is generally a function of the size of the fluid reservoir that is required. For example, an infusion pump the size of a conventional electronic pager will likely have a reservoir of about 5–20 ml. If the pump is the size of a man's wrist watch, its reservoir will hold about 5 ml. A pump the size of a nickel will have a reservoir holding about 1–2 ml. Implantable pump devices or those introduced orally or by injection through a syringe will be correspondingly smaller and only able to administer substantially smaller quantities of a liquid.

Several techniques can be used to provide a positive actuation for pumping a liquid or for producing other actions involving the application of force in a micro/miniature fluid circuit. These techniques typically rely on either thermal actuation, electrostatic actuation, or magnetic actuation, but tend to have drawbacks because they either require high power (greater than 100 mW), or a relatively high voltage (greater than 30 volts) to operate. Thermal actuation can achieve a phase change in a material such as a shape memory alloy or change the length of a member due to thermal expansion/contraction. Resistive heating can be employed to produce the temperature change. Electrostatic, electrohydrodynamic, or electro-osmosis forces can be generated by applying a voltage differential to materials. For example, if one material is a membrane, a bridging member, or a cantilever, the electrostatic bias will cause the member to move relative to an opposite member to which the bias voltage is applied. In pumps employing electrohydrodynamics, fluid is moved under the influence of an electric field. Up to 1000 volts may be required to energize electrostatic and electrohydrodynamic actuators, and the conductivity of the fluid may preclude the use of electrohydrodynamics.

Piezoelectric actuators offer another possible option, but may be limited by difficulties arising in transferring the technology from ceramics to thin films like those typically used in micro/miniature fluid circuits. Magnetic actuators typically require an electromagnetic coil and may also require a permanent magnet, which can be difficult to form in a micro/miniature fluid circuit.

As will be evident from the above discussion, currently available technology is not well suited for use in fabricating valves, flow sensors, bubble sensors, and actuators in micro/miniature fluid circuits. Accordingly, it will be apparent that a new approach is needed to achieve these functions if such fluid circuits are to be successfully commercially developed for medical and other applications.

SUMMARY OF THE INVENTION

In accord with the present invention, a monolithic fluid flow control structure is defined that includes a fluid channel extending through the fluid flow control structure between an inlet port and an outlet port. The inlet port is adapted to couple in fluid communication with a fluid reservoir from which fluid is supplied to the inlet port. A virtual valve is disposed in the fluid channel, upstream of the outlet port. The virtual valve controls fluid flow through the outlet port in response to a valve control signal applied to the virtual valve. A first pressure sensor and a second pressure sensor are included, and at least one is disposed within the fluid channel, between the inlet port and the outlet port. The first and second pressure sensor respectively produce first and second pressure signals that are employed in sensing fluid flow through the fluid flow control structure as a function of the differential pressure.

A bubble sensor is preferably provided and includes a first plate and a second plate disposed on opposite sides of the fluid channel. The first and second plates sense bubbles in a fluid flowing through the fluid channel as a function of a change in capacitance or permitivity between the plates.

Both the first pressure sensor and the second pressure sensor are preferably disposed within the fluid channel. Alternatively, the second pressure sensor is disposed downstream of the outlet port, and the first and the second pressure sensors comprise a differential pressure transducer that senses a differential between a pressure within the fluid channel and a pressure downstream of the outlet port.

The virtual valve includes at least one passage having a transverse cross-sectional dimension that is less than 5 µm. A voltage is applied to the virtual valve to bias or counter bias fluid flow through the virtual valve.

In the monolithic fluid flow control structure, the fluid channel is formed of a biologically inert material, and preferably, in a slab of silicon. In one form of the invention, the monolithic fluid control structure is sufficiently compact in size to be injected into a patient's body through a hypodermic syringe.

Another aspect of the present invention is directed to a method for controlling and monitoring fluid flow in a micro/miniature device. The steps of the method are generally consistent with the functions implemented by the elements of the monolithic fluid flow control structure discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
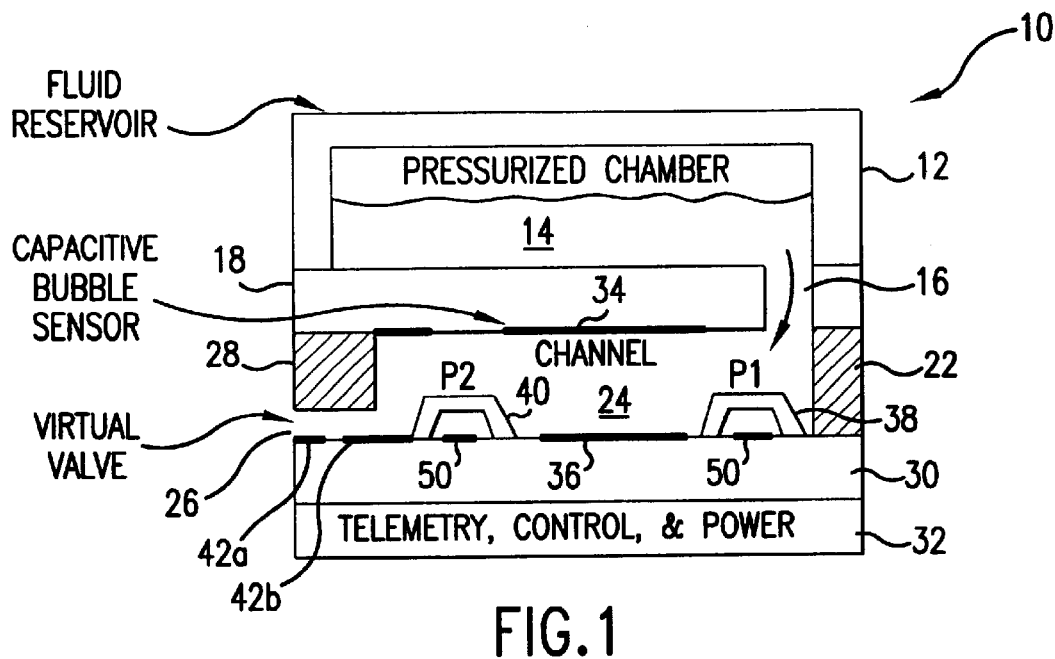
FIG. 1 is a schematic cross-sectional view of a monolithic fluid flow control unit sized to be injectable or implanted within a patient's body.

FIG. 1 illustrates a small, monolithic (fluid) flow controller 10 that is intended for administering a medicinal liquid 14. A reservoir 12 contains a small volume of the medicinal liquid and is slightly pressurized to provide a positive force used to administer the medicinal fluid to a patient after flow controller 10 is activated to enable the flow of the liquid through the device. Preferably, flow controller 10 and reservoir 12 are sized so that the area of either side, either end, or the top or bottom of the overall structure is less than 100mm$^2$. It will be appreciated that because flow controller 10 and reservoir 12 are fabricated as a monolithic structure, their overall size can readily be scaled to achieve a maximum dimension of less than 1.0 mm. An exemplary application for such a micro fluid flow control is discussed below.

Reservoir 12 is preferably formed of glass, ceramic, or other biologically compatible substances and is attached to the outer surface of a slab 18. An inlet port 16 extends through slab 18 from the interior of reservoir 12 into a channel 24 that is inside the flow controller. Slab 18 is also preferably glass, ceramic, or some other biologically inert material. Channel 24 is defined on three sides by silicon walls 22 and by a silicon block 28, which is disposed at the end of channel 24. A slab 30 formed of glass, ceramic, or other suitable biologically inert material forms the base of channel 24. A telemetry, control, and power block 32 is disposed below slab 30. Details of the telemetry, control, and power block are discussed below.

Between block 28 and slab 30 are a plurality of virtual valves 26. To control the flow of the medicinal liquid through each virtual valve, a biasing potential is applied across electrodes 42a and 42b. This biasing potential is preferably 10 volts or less. The size of the opening of each virtual valve 26 is less than 5 $\mu$m. For an opening of this size, the entry resistance is sufficiently large to prevent liquid flow through the opening unless a forward biasing voltage is applied across electrodes 42a and 42b. When a zero bias or a reverse bias is applied, liquid flow through the virtual valve is stopped. However, a forward bias voltage applied to electrodes 42a and 42b overcomes the entry resistance of the openings, enabling the medicinal liquid to flow through the virtual valve. The plurality of virtual valves 26 thus comprise an output port for the flow controller. The magnitude of the forward bias voltage that is applied to the electrodes of the virtual valves controls the rate of flow of medicinal liquid through the device. The forward biasing voltage reduces surface tension of the liquid, and that an electroosmotic force is developed by the biasing voltage that induces flow through the virtual valve.

Flow controller 10 also preferably includes a pressure sensor 38 and a pressure sensor 40 disposed at two spaced-apart points along channel 24. Pressure sensor 38 senses the pressure in channel 24 immediately adjacent inlet port 16, while pressure sensor 40 senses the pressure in the channel immediately adjacent virtual valves 26. The differential pressure drop between pressure sensor 38 and pressure sensor 40 is used to determine the rate of fluid flow through the flow controller, since the rate of flow through channel 24 is equal to the product of the differential pressure $\Delta p$ and the channel conductance C (i.e., rate of flow=$\Delta p \times C$).

On the undersurface of slab 18 in channel 24 is disposed an electrode 34. Immediately opposite electrode 34, on the opposite side of channel 24 and on the upper surface of slab 30 is disposed an electrode 36. Electrodes 34 and 36 are employed to sense variations in capacitance or permitivity of the medicinal liquid flowing through channel 24, in order to detect bubbles in the liquid. As bubbles pass between electrodes 34 and 36, the capacitance increases and the permitivity decreases. Thus, in response to changes in the permitivity or capacitance, the presence of bubbles within the medicinal liquid are readily detected. When bubbles of sufficient size/density are detected to pose a potential health risk if injected into a patient's bloodstream, virtual valves 26 can be closed with a reverse bias (or zero bias voltage) supplied by telemetry, control, and power block 32.

Figure 2:
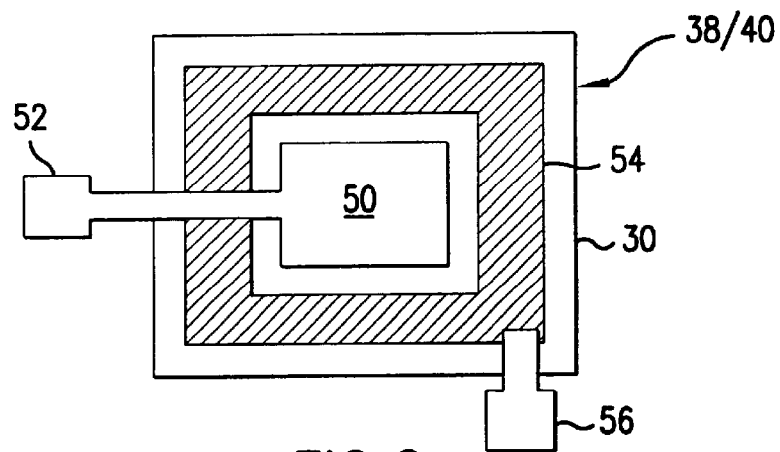
FIG. 2 is a schematic plan cross-sectional view of a capacitive pressure sensor.
Figure 3:
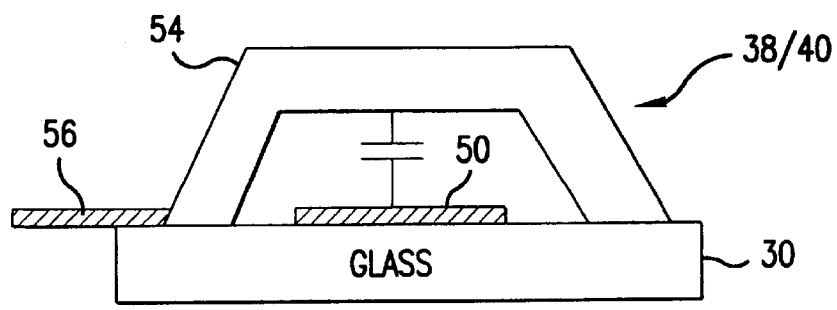
FIG. 3 is a schematic elevation cross-sectional view of the capacitive pressure sensor of FIG. 2.

Details of pressure sensors 38 or 40 are illustrated in FIGS. 2 and 3. A silicon dome 54 hermetically encloses an electrode 50 formed on the upper surface of slab 30. An electrically insulating dielectric polymer layer (not shown) is applied over a conductive trace 52 that extends from electrode 50 outwardly and beyond silicon dome 54. A second conductive trace 56 is electrically in contact with silicon dome 54 so that a capacitance exists between silicon dome 54 and electrode 50. The dielectric polymer layer applied over conductive trace 52 prevents it from electrically shorting to the silicon dome. Silicon dome 54 deflects toward electrode 50 in response to the pressure outside the dome. The deflection of the dome relative to electrode 50 changes the capacitance between the two. Thus, the capacitance between the silicon dome and electrode 50 is indicative of the pressure applied to the silicon dome by the medicinal liquid in channel 24 relative to the pressure inside the silicon dome.

Figure 4:
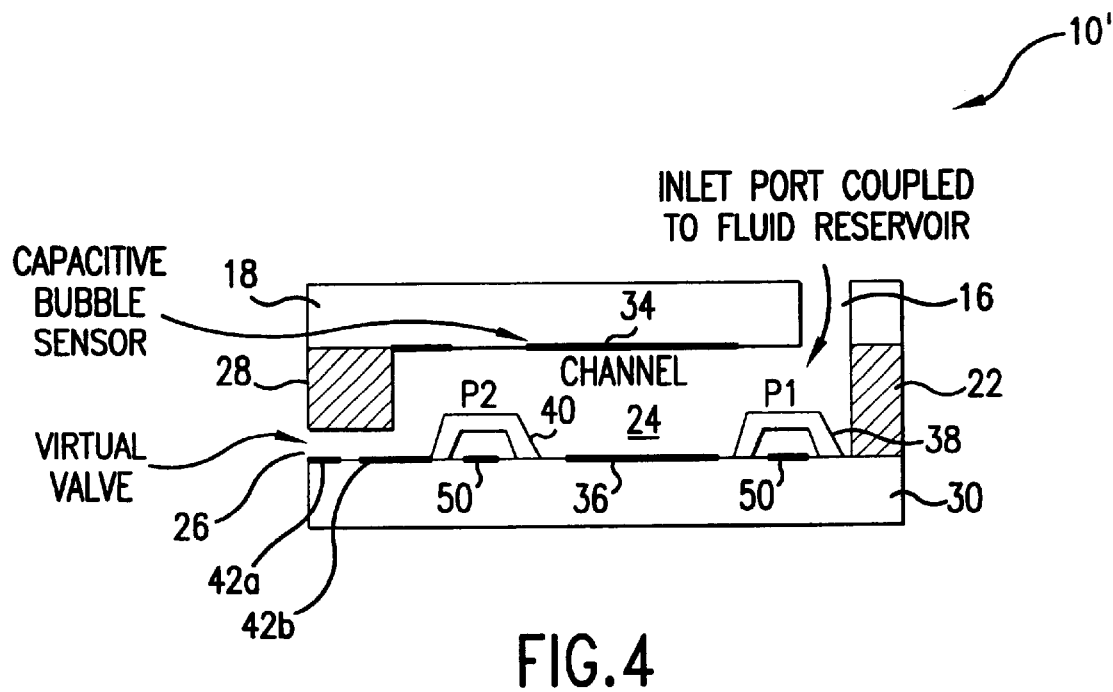
FIG. 4 is a schematic elevation cross-sectional view of a different embodiment of the monolithic fluid flow control unit.
Figure 6:
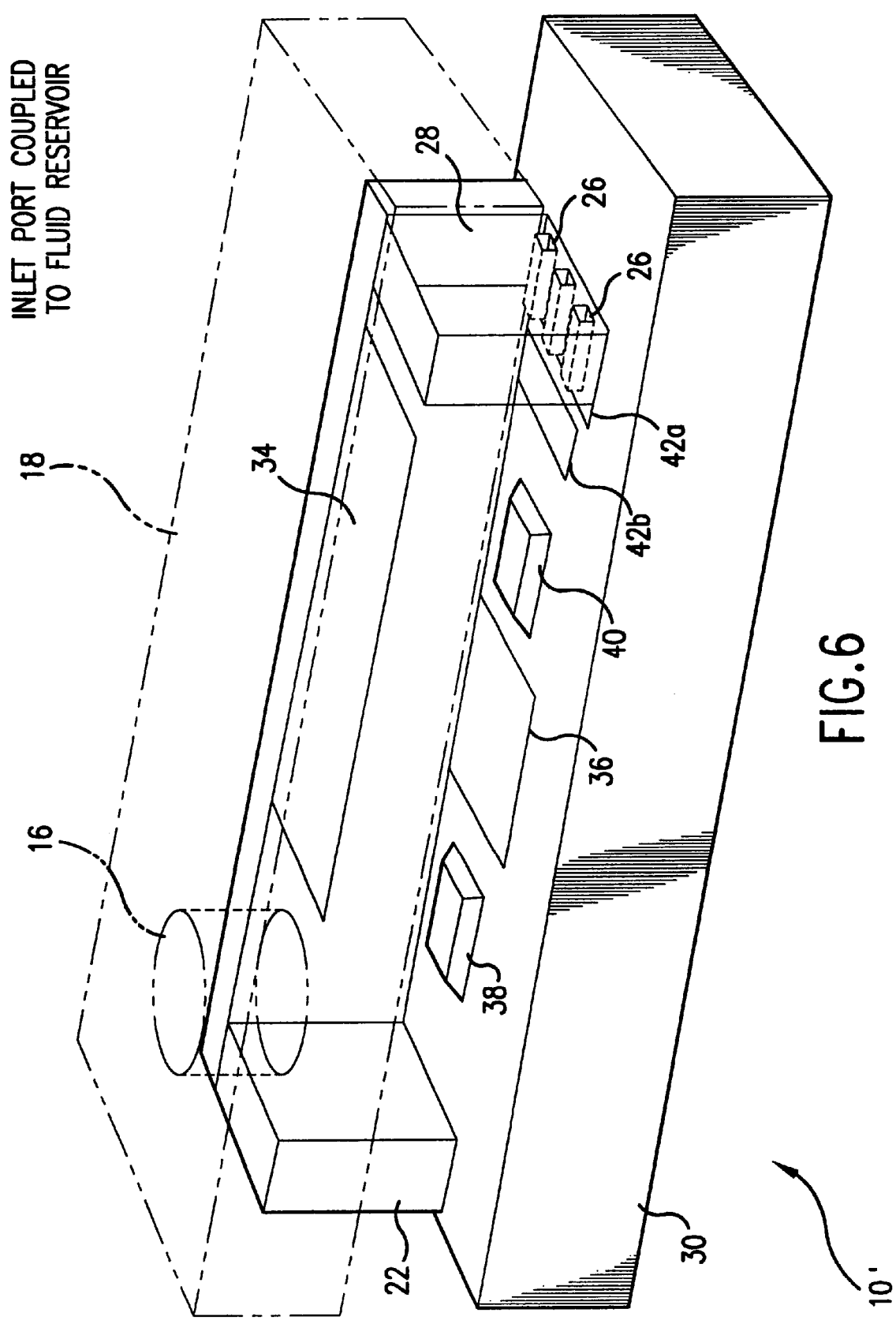
FIG. 6 is a schematic isometric view of the embodiment shown in FIGS. 4 and 5;.

With reference to FIGS. 4 and 6, a flow controller 10' is illustrated that does not include an integral fluid reservoir. Instead, inlet port 16 is coupled through a tube or otherwise is in fluid communication with a separate fluid reservoir (not shown). However, in all other respects, flow controller 10' is identical to flow controller 10, as discussed above.

Figure 5:
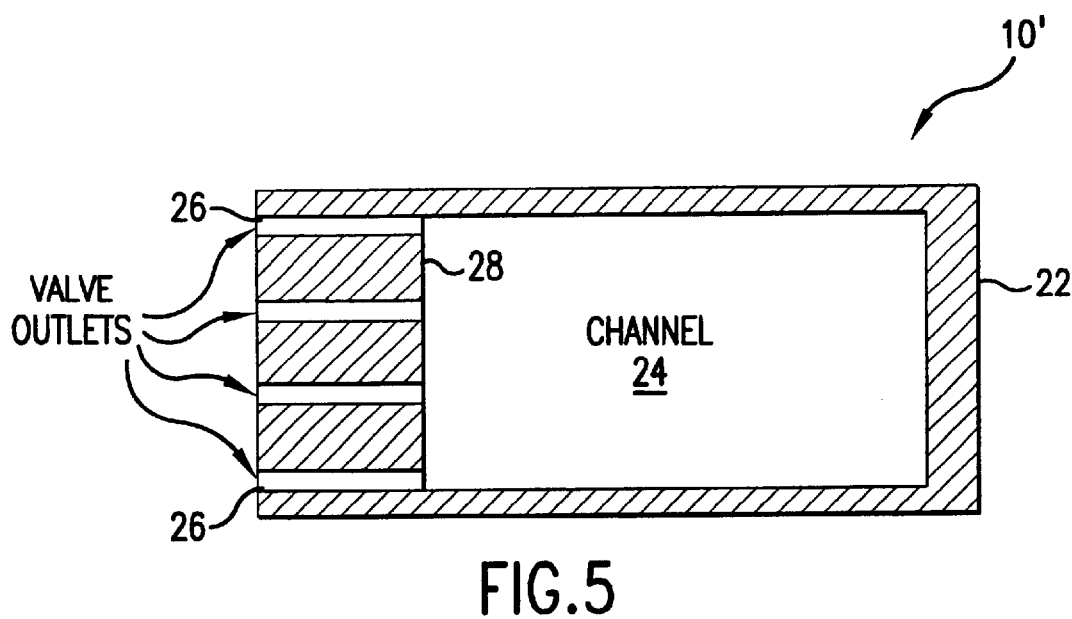
FIG. 5 is a schematic plan view of the monolithic fluid flow control unit of FIG. 4.

FIG. 5 illustrates further details of virtual valves 26. By increasing the number of virtual valves 26 formed in silicon block 28 as illustrated in FIG. 5, the total volume of flow through either flow controller 10 or 10' can be increased, compared to that possible through few virtual valve outlets. To function as a virtual valve, the cross-sectional area of each virtual valve outlet comprising virtual valves 26 must be sufficiently small to provide the restriction that prevents free flow through the virtual valve until a forward biasing voltage is applied to electrodes 42a and 42b. If less maximum flow is required, fewer virtual valves can be employed. Also, it is contemplated that the virtual valves can be selectively independently controlled to vary fluid flow through the device over a wider range or with greater resolution.

Figure 7:
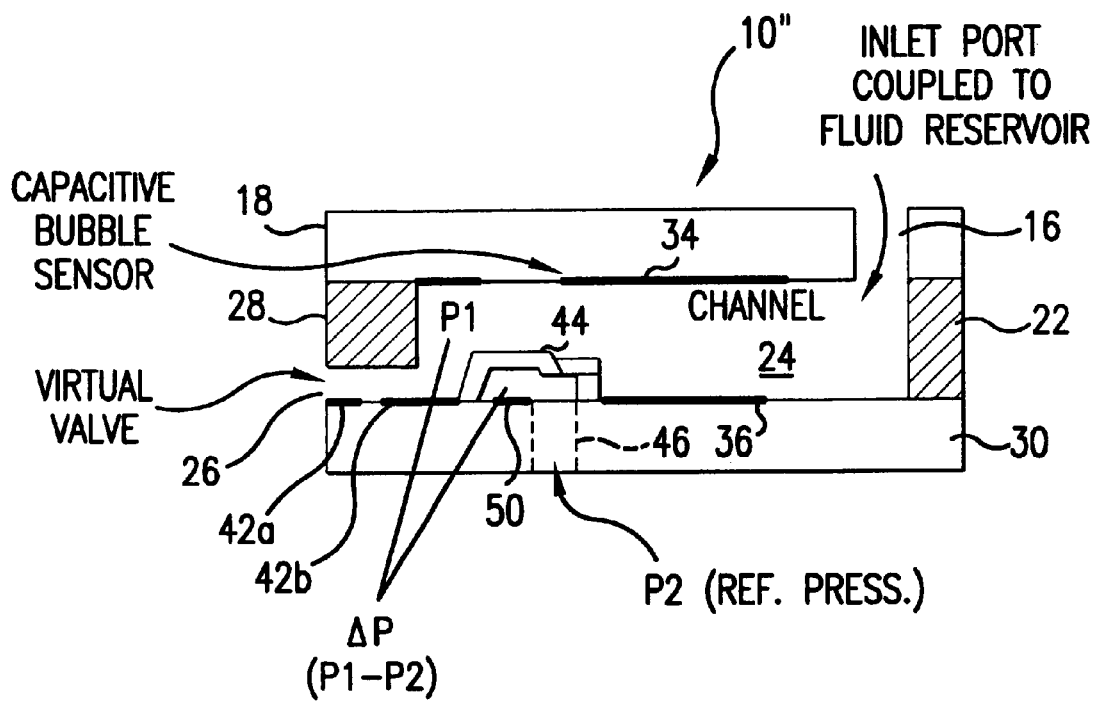
FIG. 7 is a schematic elevation cross-sectional view of a different embodiment of the monolithic fluid flow control unit.

A slightly different approach is used for monitoring fluid flow rate through the embodiment of a flow controller 10" illustrated in FIG. 7. Although flow controller 10" is shown without an integral fluid reservoir, it will be appreciated that such a reservoir can be provided, e.g., like that shown in FIG. 1. Flow controller 10" differs from flow controller 10' because it does not include two separate pressure sensors, but instead, senses the differential pressure between the medicinal fluid in channel 24 and the fluid pressure in the external environment. A differential pressure sensor 44 enables this differential pressure measurement to be made. Differential pressure sensor 44 is disposed in the same relative position as pressure sensor 40 in flow controllers 10 and 10'. A port 46 extends through slab 30 into the interior of pressure sensor 44 providing fluid communication between the external environment and the interior of the pressure sensor so that the deflection of the pressure sensor dome due to the pressure of fluid within channel 24 represents a differential pressure equal to the difference of pressure P1, which is inside channel 24, and P2, which is the pressure in the external environment. The product of the differential pressure and the conductance of channel 24 at pressure sensor 44 indicates the rate of flow of medicinal fluid through the channel. In all other respects, flow controller 10" is identical to flow controller 10'. Like flow controller 10', flow controller 10" also preferably includes a plurality of virtual valves 26 for controlling the rate of fluid flow through the device in response to the forward biasing voltage applied to electrodes 42a and 42b.

Figure 8:
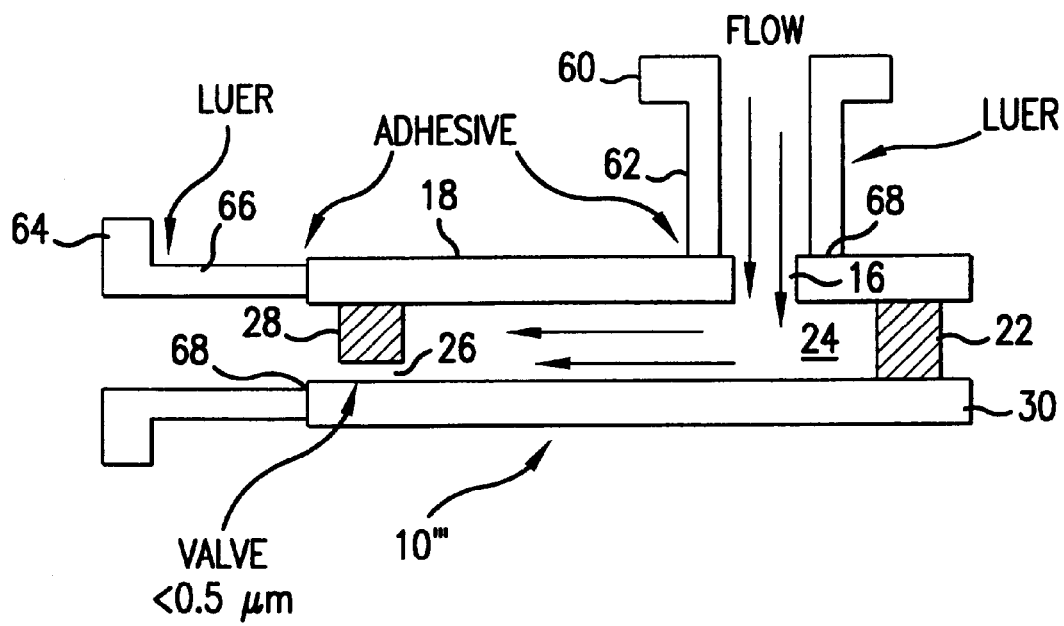
FIG. 8 is a schematic elevation cross-sectional view of yet another embodiment of the monolithic fluid flow control unit.

In FIG. 8, a flow controller 10'" is illustrated that is substantially identical to flow controller 10' with the exception that it includes a Luer fitting 62 mounted with a suitable adhesive 68 to inlet port 16. Luer fitting 62 includes a connection flange 60 for coupling to a conventional male Luer fitting (not shown) provided on a tubing that is connected to a fluid reservoir or other source of medicinal fluid (none shown). Similarly, a Luer fitting 66 is secured with an adhesive 68 to the outlet of flow controller 10''' and includes a fitting 64 for coupling to a conventional male Luer connector. Although not shown in FIG. 8, either pressure sensors 38 and 40 can be included for monitoring fluid flow rate as a function of pressure, or differential pressure sensor 44 can be included within channel 24 for this purpose. Also, electrodes (like electrodes 34 and 36) can be provided within channel 24 for monitoring the capacitance or permitivity of the medicinal liquid to detect any bubbles flowing through the channel. Alternatively, the pressure sensors and bubble sensors can be omitted from flow controller 10''', while virtual valves 26 are included to control the rate of fluid flow through the flow controller. Electrodes 42a and 42b are not shown in FIG. 8, but would be disposed within the device in a manner similar to that described above in connection with the other embodiments of the present invention. Flow controller 10''' is likely to be used externally of a patient's body for controlling fluid flow from a pump, or from a gravity fed fluid reservoir into a patient's body. In contrast with flow controllers 10, 10', and 10", flow controller 10 ''' is likely to be substantially larger to facilitate attachment of Luer fittings 62 and 66.

Figure 9:
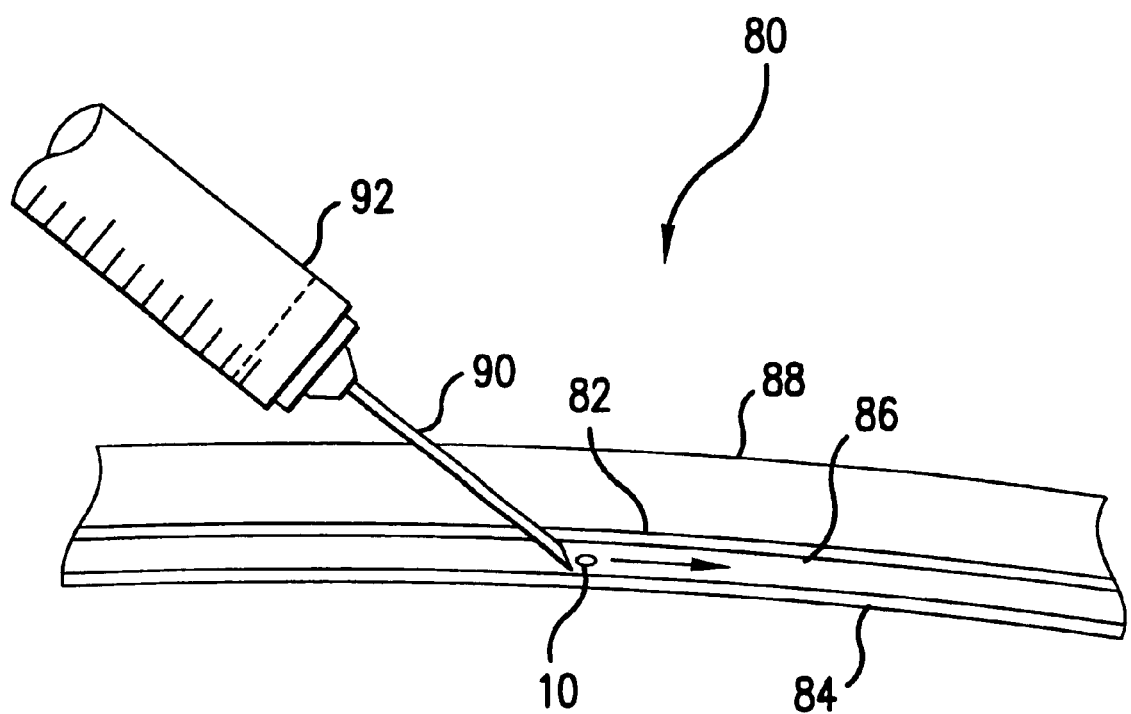
FIG. 9 is a schematic cross-sectional view of a portion of a patient's vascular system and a hypodermic syringe, illustrating the injection of the monolithic fluid flow control unit of FIG. 1.

As shown in FIG. 9, flow controller 10 is made sufficiently small so that it can be injected into a patient's blood vessel 82 through a hypodermic needle 90. Needle 90 is connected to a syringe 92 and is inserted through a dermal layer 88 and through a wall 84 of vessel 82. The flow controller is carried in a sterile fluid and is forced through needle 90 from syringe 92 into blood stream 86, which carries the device to a desired site in the body where the medicinal fluid within the integral reservoir of the device is administered to the patient.

Figure 10:
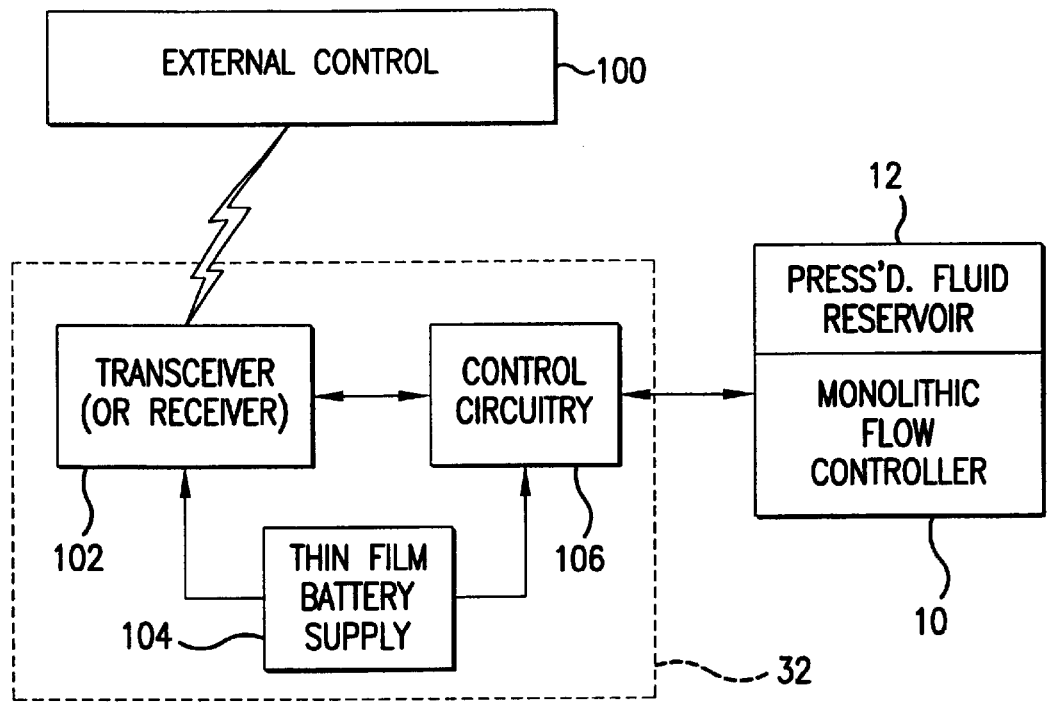
FIG. 10 is a schematic block diagram of components of the embodiment shown in FIG. 1.

Details of the circuitry or telemetry and control of flow controller 10 are illustrated in FIG. 10. As shown in this Figure, an external control 100 produces (and optionally receives) a radio signal that is received by (or transmitted from) a transceiver 102 within telemetry, control, and power block 32. Transceiver 102 can receive or transmit a simple pulse code modulated PCM signal or other modulated signal and is powered by a thin film battery supply 104, using relatively little current. Since external control 100 is preferably disposed immediately outside the patient's body, it can readily transmit radio signals to transceiver 102 and can receive relatively weak radio signals from the transceiver. In response to signals received from external control 100 by transceiver 102, a control circuit 106 controls the virtual valve in flow controller 10 to enable fluid flow and to control the rate of which fluid flows from the flow controller. If no data are transmitted to the external control by the injected or implanted device, only a receiver is required on the device. Any interruption in the delivery of the specified rate of fluid flow from flow controller 10 can be detected by control circuitry 106, which causes transceiver 102 to transmit a state signal to external control 100. For example, if bubbles are sensed in the medicinal liquid being administered to the patient by flow controller 10 causing it to stop administering the medicinal liquid, the signal transmitted to external control 100 indicates the problem, enabling medical personnel to take remedial action. Such remedial action may simply involve the insertion of another flow controller 10 within the cardiovascular system of the patient. Control circuitry 106 can also detect when all of the fluid contained within pressurized fluid reservoir 12 has been administered to the patient, and such information can be transmitted to external control 100 by transceiver 102. It is contemplated that external control 100 can be used to remotely control any embodiment of the flow controller disclosed above and to receive data from any embodiment (so long as the flow controller includes a transceiver (or receiver), and control circuitry), regardless of whether the flow controller is implanted, injected, or is used externally.

Figure 11:
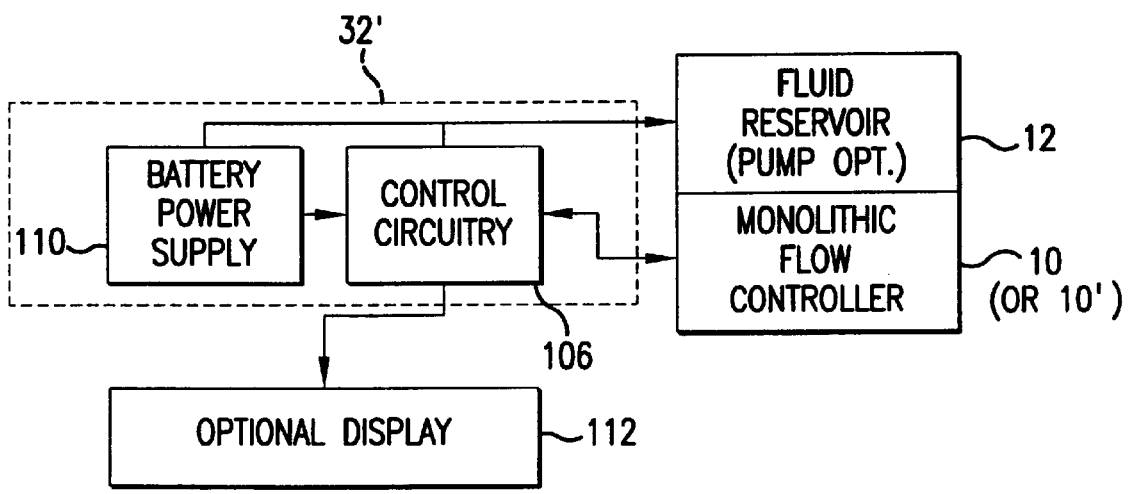
FIG. 11 is a schematic block diagram of components of any embodiment of the monolithic fluid flow control unit that is used outside a patient's body.

In FIG. 11, control and power circuit 32' is illustrated for use in connection with flow controller 10 or 10' when it is not necessary to provide for remote control and/or readout of telemetry data. In this embodiment, fluid reservoir 12, or optionally, gravity flow or an external fluid pump provides the source of fluid administered through flow controller 10 or 10'. A battery power supply 110 provides the power to energize control circuitry 106 and to drive the optional pump—if used. In addition, an optional display 112 may be coupled to the control circuitry to indicate the rate of flow and the status of the administration of medicinal fluid to the patient through the flow controller. Optional display 112 may include a liquid crystal display or other suitable electronic display, details of which are not shown. The flow controller used with control and power circuit 32' is likely to be substantially larger than that in the embodiment of FIG. 9. Accordingly, it will be more suitable for use externally of the patient's body. It should also be noted that flow controller 10''' can be employed in place of flow controller 10 or 10' in this embodiment.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A monolithic fluid flow control structure comprising:
   (a) a fluid channel extending through the fluid flow control structure between an inlet port and an outlet port, said inlet port being adapted to couple in fluid communication with a fluid reservoir from which fluid is supplied to the inlet port;
   (b) a valve disposed in the fluid channel, upstream of the outlet port, said valve controlling fluid flow through the outlet port in response to a valve control signal applied to the valve;
   (c) a first pressure sensor and a second pressure sensor, at least one of which is disposed within the fluid channel, between inlet port and the outlet port, said first and second pressure sensor producing first and second pressure signals that are employed in sensing fluid flow through said fluid flow control structure as a function of a differential pressure; and
   (d) a bubble sensor that detects bubbles within the fluid channel.

2. The monolithic fluid flow control structure of claim 1, wherein the bubble sensor includes a first plate and a second plate disposed on opposite sides of the fluid channel, said first and second plates sensing bubbles in a fluid flowing through the fluid channel as a function of a change in permitivity between the first and the second plates.

3. The monolithic fluid flow control structure of claim 1, wherein both the first pressure sensor and the second pressure sensor are disposed within the fluid channel.

4. The monolithic fluid flow control structure of claim 1, wherein the second pressure sensor is disposed downstream of the outlet port.

5. The monolithic fluid flow control structure of claim 1, wherein the first and the second pressure sensors comprise a differential pressure transducer that senses a differential between a pressure within the fluid channel and a pressure downstream of the outlet port.

6. The monolithic fluid flow control structure of claim 1, wherein the valve comprises at least one passage having a transverse cross-sectional dimension that is less than 5 $\mu$m.

7. The monolithic fluid flow control structure of claim 1, wherein the valve control signal comprises a voltage applied to the valve to bias or counter bias fluid flow through the virtual valve.

8. The monolithic fluid flow control structure of claim 1, wherein the fluid channel is formed in a slab of silicon.

9. The monolithic fluid flow control structure of claim 1, wherein the monolithic fluid control structure is sufficiently compact in size to be implanted into a patient's body through a hypodermic syringe.

10. A fluid flow control for controlling a flow of a medicinal fluid into a patient's body, comprising:
   (a) a pair of slabs between which a fluid path is defined that extends between an inlet port and an outlet port, said inlet port being adapted to couple in fluid communication with a source of the medicinal fluid, to receive the medicinal fluid through the inlet port;
   (b) flow sensing means for sensing a flow rate of the medicinal fluid along the fluid path as a function of a fluid pressure within the fluid path; and
   (c) valve means for controlling a flow of the medicinal fluid through the fluid path in response to a fluid flow control signal, the valve means comprising a bias voltage applied to a plurality of orifices, each of the plurality of orifices having a cross-sectional area sufficiently small to prevent fluid flow through each of the plurality of orifices without the presence of a forward bias voltage, wherein the flow rate through the plurality of orifices is controlled by the magnitude and direction of the bias voltage applied.

11. The fluid flow control of claim 10, wherein the flow sensing means comprise one of a pair of pressure sensors spaced apart along the fluid path for producing a pressure sensor signal indicative of the flow of the medicinal fluid through the fluid path.

12. The fluid flow control of claim 11, wherein the flow sensing means comprise a differential pressure sensor that senses a difference between a pressure in the fluid path and a pressure downstream of the outlet port.

13. The fluid flow control of claim 11, further comprising a bubble sensor that detects bubbles within the fluid path.

14. The fluid flow control of claim 13, wherein the bubble sensor includes a pair of conductive plates disposed on opposite side of the fluid path, said pair conductive plates being capacitively coupled to each other so that varying permitivity occurs as bubbles conveyed by the medicinal fluid pass through the fluid path between the pair of conductive plates.

15. The fluid flow control of claim 10, wherein each of the plurality of orifices has a transverse dimension that is less than 5 $\mu$m.

16. The fluid flow control of claim 10, wherein the inlet port extends through a surface of one of the slabs.

17. The fluid flow control of claim 10, wherein the pair of slabs are formed of a biologically compatible material.

18. A fluid flow control structure comprising:
   (a) a fluid channel extending through the fluid flow control structure between an inlet port and an outlet port, said inlet port being adapted to couple in fluid communication with a fluid reservoir from which fluid is supplied to the inlet port;
   (b) a valve for controlling fluid flow through the fluid channel as a function of a fluid pressure within the fluid channel, the valve comprising a bias voltage applied to a plurality of orifices, each of the plurality of orifices having a cross-sectional area sufficiently small to prevent fluid flow through each of the plurality of orifices without the presence of the bias voltage, wherein the flow rate through the plurality of orifices is controlled by the magnitude and direction of the bias voltage applied; and
   (c) flow sensing structure for sensing a flow rate of the fluid in the fluid channel as a function of a fluid pressure within the fluid channel.

19. The fluid flow control structure of claim 18, wherein the flow sensing structure comprises one of a pair of pressure sensors spaced apart in the fluid channel for producing a pressure sensor signal indicative of the flow of the fluid through the flow channel.

20. The fluid flow control structure of claim 18 wherein the flow sensing structure comprises a pressure sensor that senses a difference between a pressure within the fluid channel and a pressure outside of said fluid channel.

* * * * *

UNITED STATES PATENT AND TRADEMARK OFFICE
CERTIFICATE OF CORRECTION

PATENT NO. : 6,349,740 B1 Page 1 of 1
DATED : February 26, 2002
INVENTOR(S) : Steve T. Cho et al.

It is certified that error appears in the above-identified patent and that said Letters Patent is hereby corrected as shown below:

<u>Column 9,</u>
Line 12, replace "virtual valve" with -- valve --

Signed and Sealed this

Tenth Day of September, 2002

Attest:

Attesting Officer

JAMES E. ROGAN
Director of the United States Patent and Trademark Office